US012751902B2

(12) United States Patent
Mitra et al.

(10) Patent No.: US 12,751,902 B2
(45) Date of Patent: Oct. 6, 2026

(54) METHODS OF FORMING AN ENCAPSULATED CORE MATERIAL, AN ENCAPSULATED MATERIAL, COMPOSITIONS USES THEREOF

(71) Applicants: Sushanta Kumar Mitra, Waterloo (CA); Sirshendu Misra, Waterloo (CA); Utsab Banerjee, Waterloo (CA)

(72) Inventors: Sushanta Kumar Mitra, Waterloo (CA); Sirshendu Misra, Waterloo (CA); Utsab Banerjee, Waterloo (CA)

( * ) Notice: Subject to any disclaimer, the term of this patent is extended or adjusted under 35 U.S.C. 154(b) by 257 days.

(21) Appl. No.: 18/640,214

(22) Filed: Apr. 19, 2024

(65) Prior Publication Data

US 2024/0350377 A1 Oct. 24, 2024

Related U.S. Application Data

(60) Provisional application No. 63/497,617, filed on Apr. 21, 2023.

(51) Int. Cl.

| | |
|---|---|
| ***A61K 8/11*** | (2006.01) |
| ***A23L 21/25*** | (2016.01) |
| ***A23P 10/30*** | (2016.01) |
| ***A61K 9/50*** | (2006.01) |

(52) U.S. Cl.

CPC ................ *A61K 8/11* (2013.01); *A23L 21/25* (2016.08); *A23P 10/30* (2016.08); *A61K 9/5031* (2013.01); *A61K 9/5089* (2013.01); *A61K 2800/623* (2013.01); *A61K 2800/654* (2013.01)

(58) Field of Classification Search

CPC ...... A61K 8/11; A61K 9/5089; A61K 9/5031; A61K 2800/654; A61K 2800/623; A23P 10/30; A23L 21/25

See application file for complete search history.

(56) References Cited

U.S. PATENT DOCUMENTS 12,145,120 B2 * 11/2024 Mitra ...................... B01J 13/22

* cited by examiner

*Primary Examiner* — Shirley V Gembeh

(74) *Attorney, Agent, or Firm* — Dilworth & Barrese, LLP.; Michael J. Musella, Esq.

(57) ABSTRACT

The present disclosure provides a method of forming a liquid encapsulated core material and encapsulated core material compositions and uses thereof, where an interfacial fluid of a known volume is first layered on a host fluid. The encapsulated core material is then formed either by dispensing a core material from proximity, leading to the formation of a shell of interfacial material around the core material in an interfacially trapped state, or by generating a compound core material with a target inner core enclosed within a higher density outer core using a Y-junction geometry and impinging the said compound core with sufficient kinetic energy onto the floating interfacial fluid layer to form the encapsulated material via complete interfacial penetration of the compound core material.

20 Claims, 6 Drawing Sheets

METHODS OF FORMING AN ENCAPSULATED CORE MATERIAL, AN ENCAPSULATED MATERIAL, COMPOSITIONS USES THEREOF

FIELD OF INVENTION

The present disclosure relates generally to methods of encapsulating materials and to encapsulated materials produced by such methods. More particularly, the present disclosure relates to liquid encapsulation methods and compositions and uses related to thereto.

BACKGROUND

The following introduction is intended to introduce the reader to this specification but not to define or limit any invention. One or more inventions may reside in a combination or sub-combination of elements or steps described below or in other parts of this document. The inventors do not waive or disclaim their rights to any invention or inventions disclosed in this specification merely by not describing such other inventions or inventions in the claims.

Encapsulation aims to envelop a core material with at least one outer layer around it. There are different forms of encapsulation. Encapsulation may be relevant to multiple industrial applications, including pharma/nutraceuticals, agriculture, food processing, cosmetics, and efficient energy management systems. Encapsulation can shield a core material from a surrounding environment, such as in protecting enzymes from denaturing solvents, shielding a core material from oxidation, shielding a core material from moisture, and improving the delivery of bioactive molecules (e.g., antioxidants, vitamins, minerals, fatty acids, and antioxidants) and living cells (e.g., probiotics) into foods, as well as in the pharmaceutical industry, where expensive active pharmaceutical ingredients (e.g., core materials) can be protected by encapsulating inside a suitable shell. Additionally, encapsulation facilitates improved control over the release kinetics of the drugs in case of targeted drug delivery or may mask the taste and odor of certain drugs. In such examples, the capsules containing a drug may be treated as drug delivery cargo, targeting a specific lesion inside a subject's body where shell breakage may occur under suitable chemical conditions.

Encapsulation techniques can be classified into chemical, physical, physicochemical, and microfluidic-based methods. Chemical methods may include in situ polymerization; physical methods may include spray-drying and fluidized bed coating; physicochemical methods may include complex coacervation and sol-gel encapsulation. However, these processes can suffer from restrictions, including difficulty in controlling shell thickness, low yield, presence of coacervating materials on the surface of capsules, low stability of capsules, and use of relatively toxic chemicals, which may limit the utility of these conventional techniques. Despite their precision and control of morphology, microfluidics-based systems can also suffer from restrictions as they may require the fabrication of microfluidic devices, involvement of multiple syringe pumps for fluid infusion, and controlled wetting conditions. New and effective techniques for encapsulating core materials, including liquid encapsulation techniques, are desirable.

Previously demonstrated was a platform for encapsulation[1,2] where encapsulation was achieved by impact-driven entry into a host fluid of core material from an impact height H through a floating interfacial material layer of a liquid (shell). This technique was later extended[3] to include stable triple-layer encapsulation and subsequent extraction of the encapsulated material via UV-curing of the outer shell. The previous approach[1,2] for encapsulation was kinetic energy dependent and included the formation of encapsulated materials after successful interfacial penetration. Sufficient kinetic energy of the impacting core material led to the material being able to penetrate through the interfacial material layer instead of getting trapped at the interface where it could neither be cured nor be extracted/transported to another location. Further, for the previous approach, the core material, the shell, and the host fluid conformed to density conditions where the core material was the heaviest, as the encapsulated material needed to separate from the interfacial material layer and settle down at the bottom of the host fluid. The previously demonstrated approach loses applicability when the core material does not have sufficient kinetic energy to penetrate through the floating interfacial material layer, which can occur in some of the following non-limiting cases, including low impact height, low density of core material, and low volume of core material.

Described herein are two alternative methods that augment the previously demonstrated platform[1,2] and render the platform kinetic energy independent.

The first approach[4] is a method for encapsulation, comprising deliberately interfacially trapping a core material in an interfacial material layer. In an example, the interfacial material layer comprises PDMS. As described herein, complete interfacial penetration is not a prerequisite to encapsulate a core material as long as the involved liquid triplet (i.e., core material, shell, and the host fluid) adheres to an identified thermodynamic criterion. Instead, encapsulation is achieved by the core material attaining an interfacially trapped state. As a result, the method described herein may be implemented without a minimum size restriction of the core material, without a minimum impact height, and/or without density criteria, rendering the method agnostic in terms of kinetic energy requirement. Also described herein is the relevant theoretical threshold for the thermodynamic favorability of an encapsulated state in the interfacially trapped configuration. Further, the method described herein discloses a kinetic description of the interfacial interaction that leads to successful encapsulation. Additionally, the disclosed method can encapsulate and protect a target analyte (e.g., core material) in an aggressive environment, for example, by forming capsules with a water-soluble core material inside a host water bath. In an example, food ingredients (honey/maple syrup) were used to show how the herein described method may be used in the manufacture of experience-driven beverages with localized flavoring. For example, the method disclosed herein may generate honey-flavored beverages with multiple dispersed honey capsules, where the honey content is not homogeneously mixed in the bulk of the drink and instead is released only upon chewing the capsules. The method described herein may also facilitate the simultaneous encapsulation of multiple core materials of different compositions, leading to the formation of encapsulated Janus droplets with multiple functionalities. Further, owing to the usage of curable materials as the interfacial material layer (e.g., PDMS), the shell of the interfacially trapped core material may be cured by heating, enabling extraction of the encapsulated material for practical utilization. The cured capsules may withstand regular handling, which was demonstrated experimentally using compressive stress testing.

The second approach comprises deliberately enclosing the targeted core (termed the "inner core") inside a high-density carrier fluid (termed the outer core) in the form of a compound droplet using a Y-junction geometry[5], known by those of skill in the art. Subsequently, the compound droplets, consisting of an inner and outer core, are impinged on an interfacial material layer floating on the host bath, generating encapsulated materials inside the host fluid bath. The interfacial material layer may be comprised of one fluid or at least two (e.g., two or more) fluids where a first fluid is layered on a second fluid.

SUMMARY

As described herein, there is provided:

1. A method of forming an encapsulated core material, the method comprising:
   providing an interfacial material layered on a host fluid;
   dispensing a core material onto the interfacial material;
   interfacially trapping the core material in the interfacial material and
   forming a shell of interfacial material around the interfacially-trapped core material that protects the core and forms the encapsulated core material.
2. The method of embodiment 1, further comprising curing the shell of the encapsulated material while interfacially trapped by exposing the encapsulated material to heat or UV radiation, and forming a cured encapsulated material.
3. The method of embodiment 2, further comprising isolating the cured encapsulated material from the interfacial material or host fluid.
4. The method of any one of embodiments 1 to 3, wherein the core material has a density less than the density of the host fluid.
5. The method of any one of embodiments 1 to 4, wherein providing the interfacial material comprises dispensing a volume V of the interfacial material on the host fluid.
6. The method of any one of embodiments 1 to 5, wherein accelerating the core material comprises dropping the core material onto the interfacial material from a height H above the interfacial material wherein the height H is ≥0 mm, or about 0 mm to about 1000 mm, or actuating the core material onto the interfacial material.
7. The method of any one of embodiments 1 to 6, wherein dispensing the core material comprises placing the core material onto the interfacial material.
8. The method of any one of embodiments 1 to 7, wherein interfacially trapping the core material in the interfacial material requires $\gamma_{12}+\gamma_2<\gamma_1$, where $\gamma_1$ is the core material/atmosphere interfacial tension, $\gamma_{12}$ is the core material/interfacial material interfacial tension, and $\gamma_2$ is the interfacial fluid/atmosphere interfacial tension.
9. The method of any one of embodiments 1 to 8, further comprising:
   dispensing at least a second core material onto the interfacial material,
   interfacially trapping the at least second core material in the interfacial material;
   forming a shell of interfacial material around the at least second core material; and
   forming an outer shell of interfacial material around the encapsulated core material and at least second encapsulated core material to form an encapsulated material.
10. A method of forming an encapsulated core material, the method comprising:
    providing an interfacial material layered on a host fluid;
    generating a compound core droplet where the target inner core is enclosed within a high-density outer core using Y-junction geometry; and
    passing the compound core material with sufficient kinetic energy through the interfacial fluid and into the host fluid such that the interfacial fluid forms a shell around the outer core material that protects the outer and inner core and forms the encapsulated core material.
11. The method of embodiment 10, wherein the compound core material has an effective density $\rho$, the interfacial fluid has a density $\rho_2$ and host fluid has a density $\rho_3$, and wherein:

$$\rho_2 < \rho_3 < \rho$$

and $$\rho = \beta\rho_{c,i} + (1-\beta)\rho_{c,o}$$

where, $\rho_{c,i}$ and $\rho_{c,o}$ are the densities of the inner core and the outer core, respectively. Here, $\beta$ is the ratio of the volume of the inner core material to the volume of the total compound core material.
12. The method of any one of embodiments 10 to 11, wherein the formation of stably encapsulated material inside the host bath requires $\gamma_{L_{c,o}-h}-\gamma_{L_{c,o}-L_s}-\gamma_{L_s-L_h}>0$ where $\gamma_{L_{c,o}-h}$, $\gamma_{L_{c,o}-L_s}$ and $\gamma_{L_s-L_h}$ are the interfacial tension values of outer core/host bath, outer core/interfacial fluid, and interfacial fluid/host bath combinations, respectively.
13. The method of any one of embodiments 1 to 12, wherein the core material is a fluid, and the fluid comprises a liquid, a liquid mixture, a liquid polymer, a liquid polymer mixture, a laser liquid, a liquid agar gel, a liquid gelatin, a liquid cellulose, a liquid food ingredient, a liquid nutrient, an oil, a fish oil, a probiotic, a solution, a pharmaceutical compound, an enzyme, a colloidal liquid, a suspension containing microparticles, nanoparticles, a ferrofluid, a water-treatment compound, a soil-treatment compound, or a combination thereof.
14. The method of any one of embodiments 1 to 13, wherein when the core material is a solid, the solid comprises a solid mixture, a solid suspension, a gel, an agar gel, a gelatin, a polymer, a cellulose, a nut, a seed, a pharmaceutical compound, an enzyme, a microparticle, a nanoparticle, a ferrofluid, a surfactant, a mineral, a food ingredient, a nutrient, an oil, a fish oil, a probiotic, a water-treatment compound, a soil-treatment compound, or a combination thereof.
15. The method of any one of embodiments 1 to 14, wherein the interfacial material comprises a liquid, a liquid mixture, a liquid polymer, a liquid polymer mixture, a laser liquid, a liquid agar gel, a liquid gelatin, a liquid cellulose, a liquid food ingredient, a liquid nutrient, an oil, a fish oil, a probiotic, a solution, a pharmaceutical compound, an enzyme, a colloidal liquid, a suspension containing microparticles, nanoparticles, a ferrofluid, a surfactant, a mineral, a food ingredient, a water-treatment compound, a soil-treatment compound, or a combination thereof.

16. The method of any one of embodiments 1 to 15, wherein the interfacial material is curable including, but not limited to, cross-linkable or vulcanizable materials and comprises a liquid, liquid mixture, liquid polymer, liquid polymer mixture, laser liquid-liquid agar gel, liquid gelatin, liquid cellulose, oil, silicone oil, solution, suspension, colloidal liquid, ferrofluid, starch-based biopolymers, thiol-ene biopolymers, or a combination thereof.
17. The method of any one of embodiments 1 to 16, wherein the host fluid is a liquid, a liquid mixture, a liquid food ingredient, a liquid polymer, a liquid polymer mixture, a liquid agar gel, a liquid gelatin, a liquid cellulose, a liquid consumer beverage, a liquid nutrient, an oil, a silicone oil, a fish oil, a solution, a suspension, a colloidal liquid, a ferrofluid, water, an aqueous solution, or a combination thereof.
18. A method of forming a multi-layered encapsulated core material comprising a core material and a shell, the method comprising:
    providing an interfacial material layer on a host fluid, the interfacial material layer comprising a first and a second interfacial material, the first interfacial material being layered on the second interfacial material and the second interfacial material being layered on the host fluid, and
    passing the compound core material with sufficient kinetic energy through the interfacial layer and into the host fluid and
    forming a shell of the interfacial material layer around the core material, the shell comprising at least the first and second interfacial material,
    thereby forming the multi-layered encapsulated core material.
19. A cured encapsulated material, comprising:
    an encapsulated core material comprising a core material encapsulated in a shell,
    the shell comprising cured interfacial material.
20. Use of the encapsulated core material made by the method of any one of embodiments 1 to 18, or the cured encapsulated material of 19:
    for delivery of a pharmaceutical compound;
    for targeted locomotion of the encapsulated material using active stimuli (e.g., magnetic/electric field, acoustics)
    for delayed release of a pharmaceutical compound;
    in a cosmetic product;
    for delayed release of an additive in a cosmetic product;
    in an emulsion;
    for encapsulating a food ingredient;
    in a food product;
    quantum-dot light emitting diodes;
    for controlled reactions and/or
    in a beverage.
    In confectionary

BRIEF DESCRIPTION OF THE FIGURES

Embodiments of the present disclosure will now be described, by way of example only, with reference to the attached Figures.

DETAILED DESCRIPTION

Figure 1:
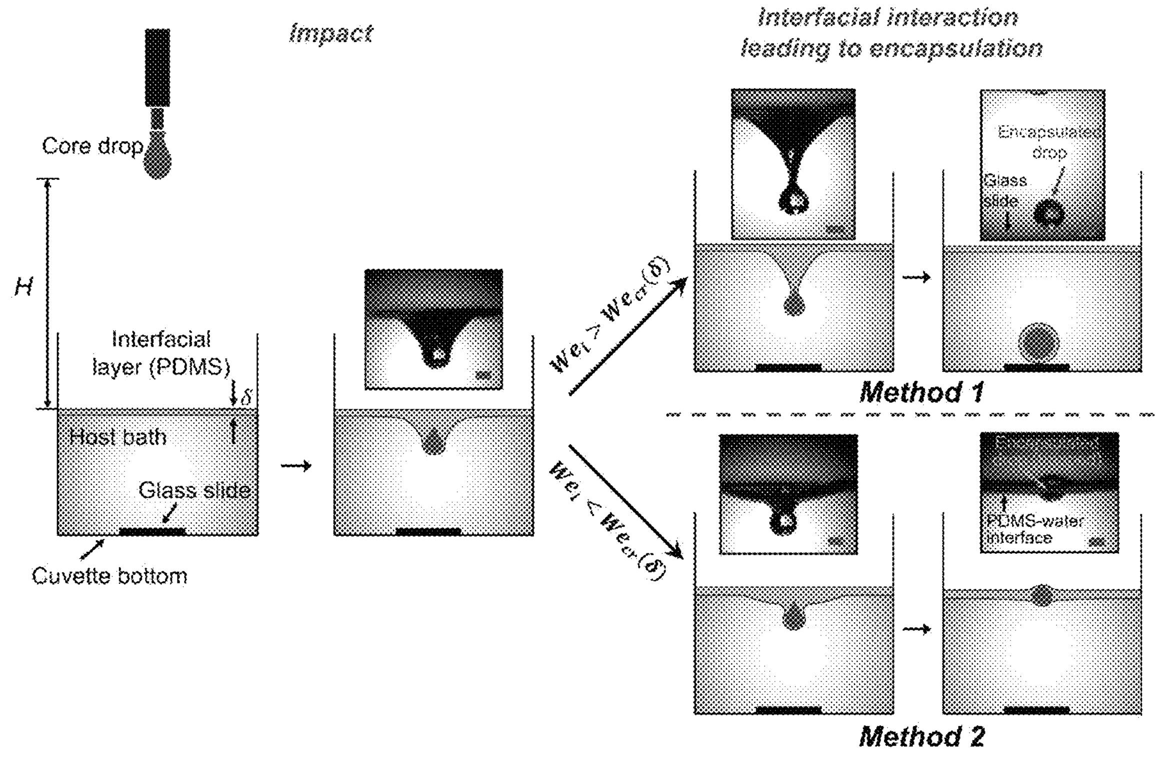
FIG. 1 depicts a schematic representation of liquid-liquid encapsulation. Method 1 depicts a necking-assisted encapsulation mechanism leading to the formation of encapsulated materials at the bottom of the cuvette. Method 2 depicts the interfacial trapping process described herein, where the oncoming core material is encapsulated and remains attached to the floating interfacial material layer. The scale bar represents 2 mm in all the experimental images of the inset.

Generally, the present disclosure relates to liquid encapsulation methods and encapsulated core materials produced by these methods. Particularly, an interfacial fluid is provided on a host fluid. Depending upon the kinetic energy, the core material either gets trapped at the interfacial material layer in an encapsulated state (Example I) or passes through the interfacial fluid and into the host fluid to form a shell of interfacial fluid around the core material (Example II). This results in the formation of an encapsulated material either at the floating interfacial material layer or at the host fluid. The core material may be a fluid or a solid. The interfacial fluid may be comprised of one fluid or comprised of at least two (e.g., two or more) fluids where a first fluid is layered on a second fluid. Any one of the interfacial fluid, host fluid, or core material may comprise an analyte. At least one use of the encapsulated materials includes delivery and/or delayed release of the analyte.

In an aspect of the present disclosure, there is provided a method of forming an encapsulated material, i.e., a liquid-encapsulated core material. The method comprises providing an interfacial fluid and a host fluid. The interfacial fluid is provided on top of a bath made of the host fluid. It will be noted that the terms liquid and fluid are used substantially interchangeably herein to refer to flowable materials. The term material is used substantially interchangeably with substance or composition in that a material may comprise one or more components. The interfacial fluid and the host fluid are selected relative to each other such that the interfacial fluid is capable of being layered on the host fluid. In accordance with the embodiment of the disclosure, the selected core material gets trapped at the interfacial material layer while being fully enclosed within the interfacial material layer in the absence of sufficient kinetic energy (Example I) or passes through the interfacial material layer to enter the host bath if the core material has sufficient kinetic energy (Example II).

As used herein, sufficient kinetic energy refers to the core material having sufficient energy, which is dependent upon its velocity, size (volume), and density, to pass through the interfacial material layer. Energy may be imparted onto the core material by any suitable means or force, including but not limited to gravity. The amount of kinetic energy required for a particular core material to pass through the interfacial fluid and into the host fluid will depend on a number of factors and can be determined by persons of skill in the art and having regard to the present disclosure. Factors to consider may include but are not limited to one or a combination of (i) composition, size, mass, shape, velocity and/or density of the core material; (ii) composition, density, and/or viscosity of the interfacial fluid; or (iii) thickness and/or interfacial energies of the interfacial layer; which are properties that may be known or determined for particular core material and interfacial fluid (e.g., see Example 1, FIG. 3); and (iv) composition, density and/or viscosity of the host fluid. Thus, sufficient kinetic energy may be determined by a person of skill in the art depending at least on the known or determined properties of the selected core material, interfacial fluid and/or host fluid, their relation to one another, and/or the method steps employed.

A suitable combination of core material, interfacial fluid and host fluid may be selected by a person of skill in the art depending on the particular objective and application. A skilled person, having regard to the present disclosure, will understand that the relative properties of the core material, the interfacial fluid, and the host fluid must be considered in selecting a combination that will result in a desired mode of successful encapsulation. As used herein, physicochemically compatible refers to the relative properties of two materials in communication with one another (e.g., the core material and the interfacial fluid and/or the interfacial fluid and the host fluid) that permit encapsulation of the core material according to the disclosed methods. For example, two physicochemically compatible materials in communication may be mutually unreactive and/or immiscible. In some embodiments, the core material and the interfacial fluid are physicochemically compatible. In some embodiments, the interfacial fluid and host fluid are physicochemically compatible. In some embodiments, the host fluid and core material are physicochemically compatible. In some embodiments, which may be combined with any of the embodiments described herein, the host fluid and the core material are not physicochemically compatible (i.e., are physicochemically incompatible) in the context of the present disclosure, e.g., they are reactive and/or are miscible relative to one another. "Miscible" or "miscibility" refers to a property of two liquids that, when mixed, provide a homogeneous solution or a single phase. In contrast, "immiscible" or "immiscibility" is a property of two liquids that, when mixed, provide a heterogeneous mixture or two distinct phases (i.e., layers).

In some embodiments involving encapsulation via interfacial trapping (Example 1), a skilled person will be able to determine the interfacial fluid and core material combination so that the spreading parameter ($S_{21}$) of the interfacial fluid on the core material is positive, where $S_{21}$ is defined as $S_{21}=\gamma_1-\gamma_2-\gamma_{12}$, where $\gamma_1$, $\gamma_2$ are the surface tension values of the core material and the interfacial fluid and $\gamma_{12}$ is the core material/interfacial fluid interfacial tension.

In some embodiments involving encapsulation via interfacial penetration of a compound core drop (Example 2), a person of skill in the art, with regard to the present disclosure, will be able to decide the volume fraction, $\beta$ of the inner core (see FIG. 6) in the compound droplet, so that the effective density of the compound drop, $\rho$ is higher than the densities of the interfacial fluid and the host fluids. $\rho$ is given as $$\rho = \beta\rho_{c,i} + (1-\beta)\rho_{c,o}$$

where, $\rho_{c,i}$ and $\rho_{c,o}$ are the densities of the inner core and the outer core material, respectively.

In some embodiments involving encapsulation via interfacial penetration of a compound core drop (Example 2), a person of skill in the art, with regard to the present disclosure, will be able to select the outer core liquid, the interfacial fluid and the host fluid such that the criteria for stability of the encapsulated material inside the host fluid, i.e., $\rho_{L_{c,o\_h}}-\gamma_{L_{c,o}-L_s}-\gamma_{L_s-L_h}>0$ where, $\gamma_{L_{c,o}-h}$, $\gamma_{L_{c,o}-L_s}$ and $\gamma_{L_s-L_h}$ are the interfacial tension values of outer core/host bath, outer core/interfacial fluid, interfacial fluid/host bath combinations, respectively.

Depending on the desired mode of encapsulation (i.e., interfacial trapping or complete interfacial penetration), a skilled person, having regard to the present disclosure, will be able to identify whether to dispense the core material proximally onto the interfacial layer or drop it from a vertical separation H.

In some embodiments, the interfacial fluid is a curable material that includes, but is not limited to, cross-linkable or vulcanizable materials. In such examples, the interfacial fluid may comprise a biocompatible photopolymer, heat-curable polymer, cross-linkable epoxy resin, or resin-based composite (e.g., a dental composite resin).

In certain embodiments of the method described herein, forming the encapsulated material may further comprise hardening the shell. In some examples, hardening the shell comprises curing the shell to form a hardened shell. In some examples, curing the shell comprises exposing the shell to heat or ultraviolet radiation. In such examples, the shell may comprise a biocompatible photopolymer, heat-curable polymer, cross-linkable epoxy resin, or resin-based composite (e.g., a dental composite resin).

In some embodiments of the method described herein, the interfacial material layer may comprise at least a first and a second interfacial fluid, the first interfacial fluid being layered on the second interfacial fluid, and the second interfacial fluid being layered on the host fluid and the core material is encapsulated with a first shell formed from the first interfacial fluid, and the first shell is encapsulated with a second shell formed from the second interfacial fluid.

To gain a better understanding of the invention described herein, the following examples are set forth. It should be understood that these examples are for illustrative purposes only. Therefore, they should not limit the scope of this invention in any way.

Definitions

Unless defined otherwise, all technical and scientific terms used herein have the meaning as commonly understood in art.

As used in the specification and claims, the singular forms "a", "an" and "the" include plural references unless the context dictates otherwise.

EXAMPLES

Example 1—Liquid-Liquid Encapsulation Via Interface Trapping Method

Materials

Three liquids were used and denoted as follows: core material (liquid $L_1$), interfacial material forming the shell (liquid $L_2$), and host fluid (liquid $L_3$), on top of which the interfacial material was dispensed. If not otherwise mentioned, a class of laser liquid—a mixture of silicanes and polyphenol ethers with a water solubility of <0.1% (Product Code: 57B63, Cargille Laboratories Inc., Cedar Grove, NJ, USA) was used to form the core material. The relevant material properties are as follows: density $\rho_1=1900$ kg/m$^3$, dynamic viscosity $\mu_1=1024$ mPa-s, liquid-air surface tension $\gamma_1=50$ mN/m, and liquid-water interfacial tension $\gamma_{13}=39.4$ mN/m. Polydimethylsiloxane (PDMS) (Sylgard 184, Dow Chemicals) was prepared by mixing the base elastomer and cross-linker in a 10:1 weight ratio and used to form the interfacial material layer. The relevant thermophysical properties are as follows: density $\rho_2=965$ kg/m$^3$, dynamic viscosity $\mu_2=3500$ mPa-s, and liquid-air surface tension $\gamma_2=22$ mN/m. The interfacial tension between $L_1$ (laser oil) and $L_2$ (PDMS), $\gamma_{12}=5.67$ mN/m was calculated using the interfacial tension formula for non-polar liquids as $\gamma_{12}=\gamma_1+\gamma_2-2\sqrt{\gamma_1\gamma_2}$. The host liquid was deionized (DI) water (purified by Milli-Q, MilliPoreSigma, Ontario, Canada) with density $\rho_3=1000$ kg/m$^3$, dynamic viscosity $\mu_3=1$ mPa-s and liquid-air surface tension $\gamma_3=72$ mN/m.

The experiments were conducted in a distortion-free glass cuvette (Product Code: SC-02, Krüss GmbH, Hamburg, Germany) of inner dimension 36 mm×36 mm×30 mm with a 2.5 mm wall thickness. Polished and stainless-steel disposable needle tips with gauge 14 and inner diameter of 0.060" (Part No. 7018035, Nordson EFD, East Province, RI, USA) mounted on 1 ml NORM-JECT® sterile luer-slip syringes (Henke-Sass, Wolf GmbH, Tuttlingen, Germany) were used for dispensing the liquids. The dispenser was mounted on a linear translating stage (A-BLQ0595, Zaber), which controlled dispersion height. Honey, maple syrup, and polyethylene glycol-based water-soluble ferrofluid were used as the core materials to demonstrate practical use cases. The ferrofluid (PBG 900, density 1860 kg/m$^3$) was purchased from Ferrotec, USA, and diluted 10-fold with DI water before experiments. Honey and maple syrup were purchased from Walmart, Canada, and used as purchased.

Methods

Before each experiment, a glass cuvette was cleaned by first dipping it in a glass beaker containing hexane and then by ultrasonication (Branson 5800, Emerson Electric Co., USA) in hexane for 30 minutes. The cuvette was then rinsed with DI water, before drying with compressed nitrogen. Next, a freshly plasma-cleaned glass slide (thickness 1 mm) was placed at the bottom of the experimental cuvette to allow easy retrieval of the encapsulated material (e.g., one or more encapsulated core materials) from the experimental cuvette. The cuvette was then partially filled with 20 ml of DI water. To prepare the interfacial material, first, the base elastomer and the curing agent were thoroughly mixed in a 10:1 weight ratio. Then, the mixture was degassed in a desiccator to remove trapped air bubbles. Subsequently, a predetermined volume of PDMS, $V_{PDMS}$ in the range of 30-1000 μl was dispensed on top of the water bath (host fluid) from close proximity using a 1 ml syringe and allowed to spread uniformly[6] for ~2 minutes resulting in the formation of a thin PDMS layer of uniform thickness, $\delta=V_{PDMS}/A_C$, where $A_C$ is the inner cross-sectional area of the cuvette Using the linear translating stage, the dispenser was then taken to the predetermined height, H. The core material was generated thereafter by slowly pumping the liquid $L_1$ through the syringe pump mounted on the dispenser. The core material's average volume for laser oil was 15.5 μL with a standard deviation of 0.8 μL. Assuming spherical geometry, this average volume corresponded to a radius of 1.54 mm, which is below the system's capillary length scale. Upon detachment from the needle, the core material came in contact with the interfacial material layer of liquid $L_2$. In the previous approach[1], referred to herein as Method 1, where the core material has sufficient kinetic energy to overcome the interfacial and viscous barrier, which assists the core material in penetrating through this interfacial material layer, it was encapsulated with a liquid layer of $L_2$ as it separated from the interfacial material layer (Method 1, FIG. 1). In contrast, the method as described herein, also referred to as Method 2, involves dispensing the core material such that it does not penetrate through the interfacial material layer. In this case, the core material becomes trapped at the interface and remains encapsulated (Method 2, FIG. 1). A step-wise schematic representation of the impact-driven encapsulation process is provided in FIG. 1. The complete dynamics of the encapsulation process were captured using a high-speed camera (Photron, FASTCAM mini) coupled with a lens interfaced with a personal computer at 6400 fps.

To cure the encapsulated material, experiments were conducted on top of a hot plate (preheated at 70° C.). Following encapsulation, the experimental cuvette containing the host fluid, floating interfacial material, and the encapsulated material was left undisturbed overnight on the hot plate at 70° C., which allowed solidification of the PDMS shell and subsequent extraction of the encapsulated material. The reusable cuvette was cleaned thoroughly between two subsequent curing experiments. After curing the encapsulated material, the cuvette was cleaned using hexane and then exposed to air plasma (PE-25, PLASMA ETCH, USA). Cleaning the cuvettes using hexane facilitates the removal of PDMS residues from the cuvette's wall, which was found to otherwise interfere with the spreading behavior of the PDMS interfacial material on the host fluid in subsequent uses, as it can lead to local roughness features and consequent spatially varying wettability along the cuvette walls. Exposing the cuvette to air plasma facilitates the uniform spreading of the interfacial material layer on the host fluid. The compression testing of the cured capsules was performed using a tribometer (CETR UMT-2, Bruker).

Results and Discussion

For comparison purposes only, the following discusses the previously reported approach[1], referred to herein as Method 1, relative to the herein-described encapsulation method, also referred to as Method 2.

In the method described herein (e.g., Method 2, FIG. 1), the core material was dispensed from a vertical separation H onto an interfacial material layer (e.g., PDMS) floating on top of a host fluid bath. When dropping the core material from a sufficiently high vertical separation H, the core material was imparted with sufficient kinetic energy to overcome viscous and interfacial resistance offered by the floating interfacial material (e.g., PDMS), the core material penetrated through the PDMS layer (e.g., Method 1, FIG. 1). When dispensing the core material onto the interfacial material, the core material became trapped at the interface of the interfacial material and host fluid because the kinetic energy was sufficiently dissipated by viscous resistance before the core material could detach from the interface (e.g., Method 2, FIG. 1).

In the context of Methods 1 and 2, kinetic energy can be reflected in terms of impact Weber number $We_i$ and the thickness of the interfacial material layer δ. The impact Weber number ($We_i$) is defined as $$We_i = \frac{\rho_1 v^2 R_c}{\gamma_1} \approx \frac{2gH\rho_1 R_c}{\gamma_1},$$

where v is the velocity of the core material just before the core material contacts the interfacial material layer, $R_c$ is the radius of the core material assuming spherical geometry, and g is the acceleration due to gravity. For a particular δ, if $We_i$ is higher than a critical Weber number $We_{cr}$ (δ), impact results in complete separation of the impinging core material from the interfacial material layer, while $We_i<We_{cr}$ (δ) leads to interfacial trapping. Subject to adherence to a favorable thermodynamic threshold, the core material is encapsulated by the interfacial material layer in both cases. Encapsulation of the core material via the first path involving complete detachment of the impinging core material from the interfacial material layer and subsequent under-liquid formation of the standalone encapsulated material is termed Method 1. In contrast, encapsulation via the second route involving interfacial trapping is named Method 2.

Mechanism Governing Encapsulation

The encapsulation method described herein (e.g., Method 2) is interfacial energy driven. In comparison, previously reported[1] encapsulation Method 1 is impact driven. Both methods involve an interplay between interfacial (surface) tension forces, viscous forces, and momentum at the four fluids (namely, air, interfacial material layer, host fluid, and the core material) interface.

Figure 2:
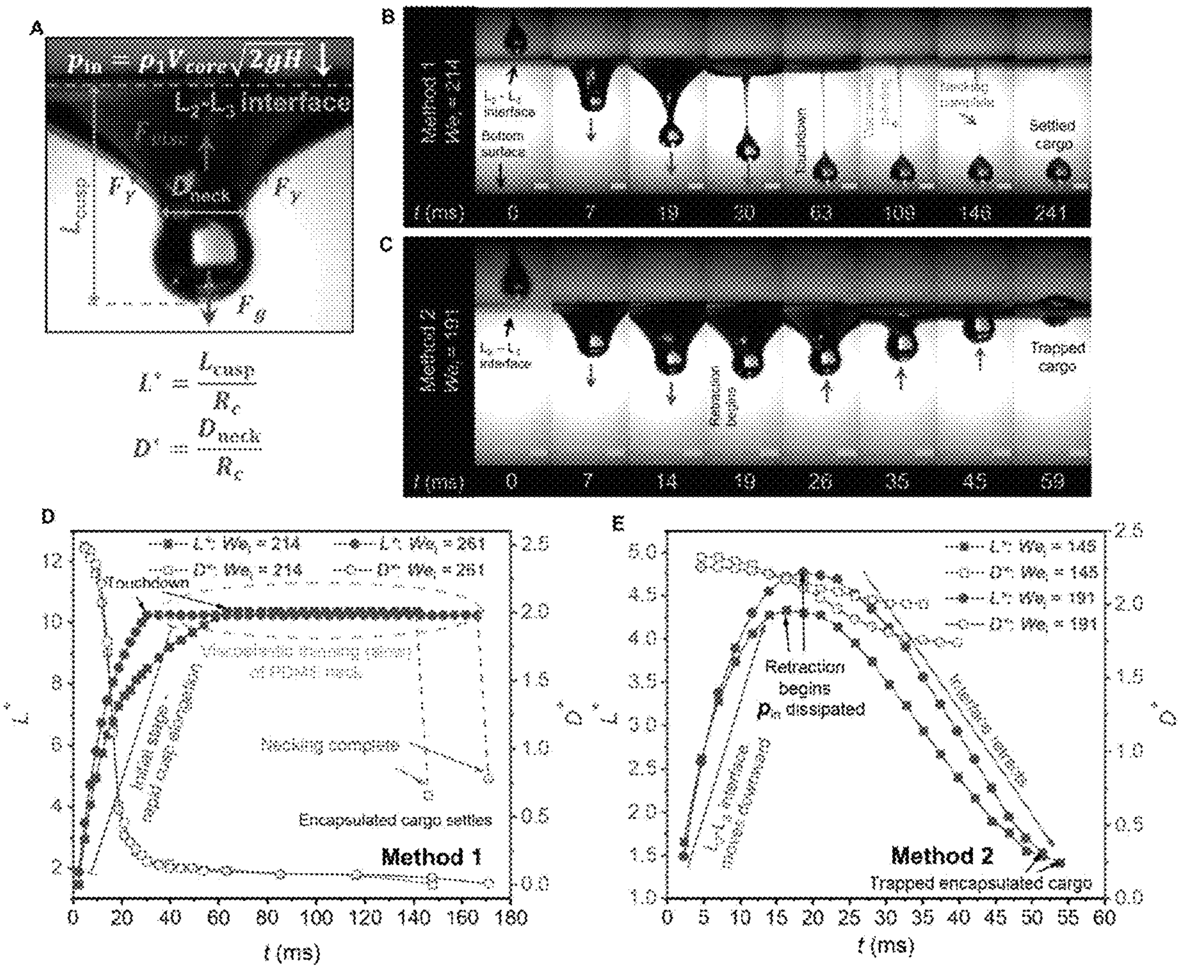
FIG. 2 depicts a kinetic description of the encapsulation process. (A) shows competing forces and consequent geometry of the neck in terms of the cusp length ($L_{cusp}$) and neck diameter ($D_{neck}$) on a typical experimental snap. (B-C) depicts the interface evolution leading to the encapsulated material formation in a time series for Method 1 and Method 2 of FIG. 1, respectively, with a scale bar of 2 mm. The $L_2$-$L_3$ interface indicated by arrows in the first snaps of both (B) and (C) denotes the unperturbed state of the interface before the impact of the core material. Upon impact, arrows mark the direction of motion of the $L_2$-$L_3$ interface over time with respect to each snap. The downward arrows denote the downward motion of the interface, while the upward arrows indicate the retraction of the interface. (D-E) provides a kinetic description of the encapsulation process in terms of the temporal variation of the non-dimensionalized cusp length ($L^*$) and the neck diameter ($D^*$) for both Method 1 and Method 2, respectively, for two different $We_i$ in each case. $V_{PDMS}$=50 µl for all the reported experiments in this figure, which corresponds to δ=38.6 µm.

The involved competing forces are schematically shown in FIG. 2A. Owing to the vertical separation H between the interfacial material layer ($L_2$) and the dispensing needle, the core material gains kinetic energy, so termed hereafter as the kinetic energy of impact ($KE_{impact}$), before it comes in contact with the interfacial material layer (e.g., PDMS). The core material has an associated initial momentum $p_{in}$ at the moment of impact, defined by $p_{in}=\rho_1 V_{core} v$, where $V_{core}$ is the volume of the core material. Upon contact, the core material attempts to penetrate through the interfacial material layer. At this point, the core material drags the interfacial material ($L_2$) layer downward through the water ($L_3$) bath (host fluid) due to its momentum $p_{in}$ which deforms the PDMS-water interface and increases its surface area. The downward-acting gravitational force, $F_g$ assists in the downward motion of the core material. However, interfacial forces, $F_\gamma$ acting on the deformed $L_2$-$L_3$ interface, attempt to restore the interface to its original position to minimize the interfacial energy. Further, the viscous force, $F_{visc}$ offered by the interfacial material layer also opposes the downward motion of the core material by dissipating its momentum. This competition leads to neck formation. The geometry of the neck may be described in terms of two characteristic non-dimensional parameters: non-dimensional cusp length L* and non-dimensional neck diameter D*, as shown in FIG. 2A. L* is defined as $L^*=L_{cusp}/R_c$, where, $L_{cusp}$ is the vertical separation of the lowest point of $L_3$-$L_2$ interface and the location of the $L_2$-$L_3$ interface in its unperturbed state (before impact). D*, is defined as $D^*=D_{neck}/R_c$, where, $D_{neck}$ is the width of the neck formed by the deformed $L_2$-$L_3$ interface, as shown in FIG. 2A. The neck represents the point of inflection of the $L_2$-$L_3$ interface where the curvature of the interface switches sign. Above the neck, the curvature of the interface is directed concave downward, while it is concave upwards below the neck. In other words, the neck is the location of zero Laplace pressure due to zero local curvature.

Competition between the three forces described above dictates the core material's fate, which involves encapsulation either by necking-driven interfacial penetration (e.g., Method 1) or by trapping at the PDMS-water interface (e.g., the interface between the interfacial material layer and the host fluid; herein described Method 2). An example of the underlying interfacial evolution corresponding to the outcomes in Method 1 and Method 2 is shown as time-resolved (high-speed) experimental snapshots in FIGS. 2B and 2C. If the core material has sufficient momentum to overcome the barrier imposed by both the interfacial forces and the viscous resistance, the core material can penetrate through the interfacial material layer ($L_2$). In this process, the core material detaches a part of the film from the interfacial material layer. This detached part of the interfacial material layer forms a thin enclosure (the encapsulating shell) around the core material. Once the encapsulated core material separates from the interfacial material layer, the residual interfacial material layer returns to its unperturbed state. This pathway is termed Method 1 (FIG. 2B).

A dispensed core material has a different outcome due to insufficient kinetic energy for penetrating through the interfacial material layer, as shown in FIG. 2C. Although the core material initially tries to separate from the interfacial material layer by elongating the $L_2$-$L_3$ interface, it fails in attaining a complete separation from $L_2$ because of the lack of, or the dissipation of $KE_{impact}$ before separation. As a result, the core material returns to the host fluid-air interface while being trapped in the interfacial material layer. In the trapped state, the core material remains wrapped all around by the interfacial material layer, as the wrapped configuration is energetically favorable (e.g., possesses lower Gibbs free energy) than its competing counter-state where the core material simply rests on the floating interfacial material layer with its top surface exposed to air. The two possible competing states translates to a thermodynamic requirement $\gamma_{12}+\gamma_2-\gamma_1<0$. For example, for the interfacially trapped state to be thermodynamically feasible, $L_2$ (interfacial material) should spread on top of $L_1$ (oncoming core material), not vice-versa. This translates to the thermodynamic requirement that the spreading parameter of $L_2$ on $L_1$ should be positive, while the spreading parameter of $L_1$ on $L_2$ should be negative. As an example, the liquid triplet, laser oil (core material, $L_1$), PDMS (shell, $L_2$), and water (host fluid, $L_3$) satisfies this criterion as (50–22—5.67) mN/m=22.33 mN/m>0. This example indicated the thermodynamic feasibility of an encapsulated state even in the interfacially trapped configuration. It may also be demonstrated by the non-coalescence of multiple identical/miscible core materials. This pathway towards encapsulation via interfacial trapping is identified as Method 2 (FIG. 2C).

FIGS. 2D and 2E depict a kinetic description of the encapsulation dynamics of Method 1 and Method 2, respectively, each in a plot of the temporal evolution of L* and D*. FIG. 2D depicts the encapsulation process via Method 1 for two different $We_i$, where the PDMS interfacial material layer ($L_2$) thickness is fixed at δ=38.6 μm. The process leading to encapsulation in Method 1 can be split into two sequential steps: rapid elongation of the PDMS interfacial material layer cusp and viscoelastic neck thinning, leading to complete separation of the encapsulated core material from the interfacial material layer, as shown in FIG. 2D. Immediately upon impact with the interfacial material layer, the core material moves fast through the interfacial material layer as the magnitude of $KE_{impact}$ dominates over the viscous and interfacial forces. As a result, the PDMS-water cusp undergoes a rapid elongation, as confirmed by the fast-increasing trend of L* with time. It also leads to fast neck thinning, manifested in an associated sharp decrease in D*. This stage continues until the $L_2$-$L_3$ interface touches the glass slide at the bottom of the cuvette. This point is marked in the relevant timestamp t~63 ms in both FIGS. 2B and 2D as 'touchdown.' For $We_i$=214, the touchdown happens at t~63 ms, while for $We_i$=261, it takes a lesser time, t~30 ms, due to a higher value of $KE_{impact}$. Evidently, $L_{cusp}$ cannot elongate any further once the touchdown happens. Therefore, following the touchdown, L* remains constant. However, at this stage, the neck undergoes a slow thinning process. This is due to the time-dependent straining behavior of the viscoelastic behavior of the interfacial layer material (PDMS), which results in the viscoelastic thinning of the PDMS neck. Finally, the neck thins beyond a critical thickness, separating the encapsulated core material from the interfacial material layer (timestamps, t~171 ms for $We_i$=261 and t~146 ms for $We_i$=214). As seen in FIG. 2D, for a fixed δ, the viscoelastic thinning happens faster if $We_i$ is lower. For $We_i$=261, the viscoelastic thinning stage (defined as the gap between the touchdown and the completion of necking) lasts for ~141 ms, while the duration is ~83 ms for $We_i$=214. It could be attributed to two possible reasons. First, a higher $KE_{impact}$ associated with higher $We_i$ leads to a faster touchdown which corresponds to a higher value of D* at the point of touchdown. For example, at $We_i$=261, D*~0.17 at touchdown (t~30 ms) while D*~0.11 when the $L_2$-$L_3$ interface touches down the bottom of the cuvette for $We_i$=214 (corresponding t~63 ms). As a result, at a higher impact Weber number, the slow viscoelastic thinning stage constitutes a higher fraction of the total neck thinning process (e.g., for $We_i$=261, ~6.7% of neck thinning takes place in the viscoelastic thinning regime, compared to ~4.4% for $We_i$=214). A second possible factor is a higher associated value of remaining downward momentum at higher $We_i$ just before the touchdown, which, once the core material encounters the bottom surface and comes to rest, gets converted into an upward-directed reaction force and slows down the necking process.

FIG. 2E depicts a kinetic description of the encapsulation process in Method 2 for two different $We_i$ with $V_{PDMS}$=50 μl and a corresponding δ=38.6 μm. As can be seen from a side-by-side comparison between FIGS. 2D and 2E, the first kinetic dynamics in both Method 1 and Method 2 may be similar. Upon impact, the core material can drag the $L_2$-$L_3$ interface downward due to its momentum. For $We_i$=191, a downward motion of the interface was observed for about t~19 ms, while the $L_2$-$L_3$ interface elongated downward for t~16.4 ms for $We_i$=145. Once the viscous and interfacial resistance dissipated initial momentum ($p_i$) of the core material, the interface started to return to its undeformed state (before impact) owing to the restorative interfacial tension forces. The onset of interface retraction is marked by arrows t~17.5 ms for $We_i$=145 and t~19 ms for $We_i$=191 on the L* vs. t plot for both the $We_i$ values in FIG. 2E. The direction reversal of the motion of the $L_2$-$L_3$ is also marked by arrow on the relevant timestamp t~19 ms for $We_i$=191 in FIG. 2C. Note that the neck thinning significantly slows down once the interface material starts retracting. The slight reduction in D*, even beyond the onset of interface retraction, could be attributed to viscoelastic effects exhibited by the PDMS interfacial material layer. Finally, the interface reinstates to its unperturbed position, with the core material trapped inside the interfacial material layer, as shown in FIG. 2B (corresponding timestamp, t~59 ms). Note that, despite a lower $KE_{impact}$, the total encapsulation time is lower in Method 2 compared to Method 1. As can be seen from FIGS. 2B and 2D, encapsulation via method 1 takes ~146 ms for $We_i$=214, while successful encapsulation is achieved in the trapped configuration (Method 2) within ~59 ms for a lower $We_i$=191. This may be due to the fact that successful encapsulation is achieved in Method 1 only after a slow viscoelastic neck thinning stage and subsequent separation of the encapsulated core material from the interfacial material layer, which is absent in Method 2.).

Regime Map of Applicability of Method 1 vs. Method 2

Figure 3:
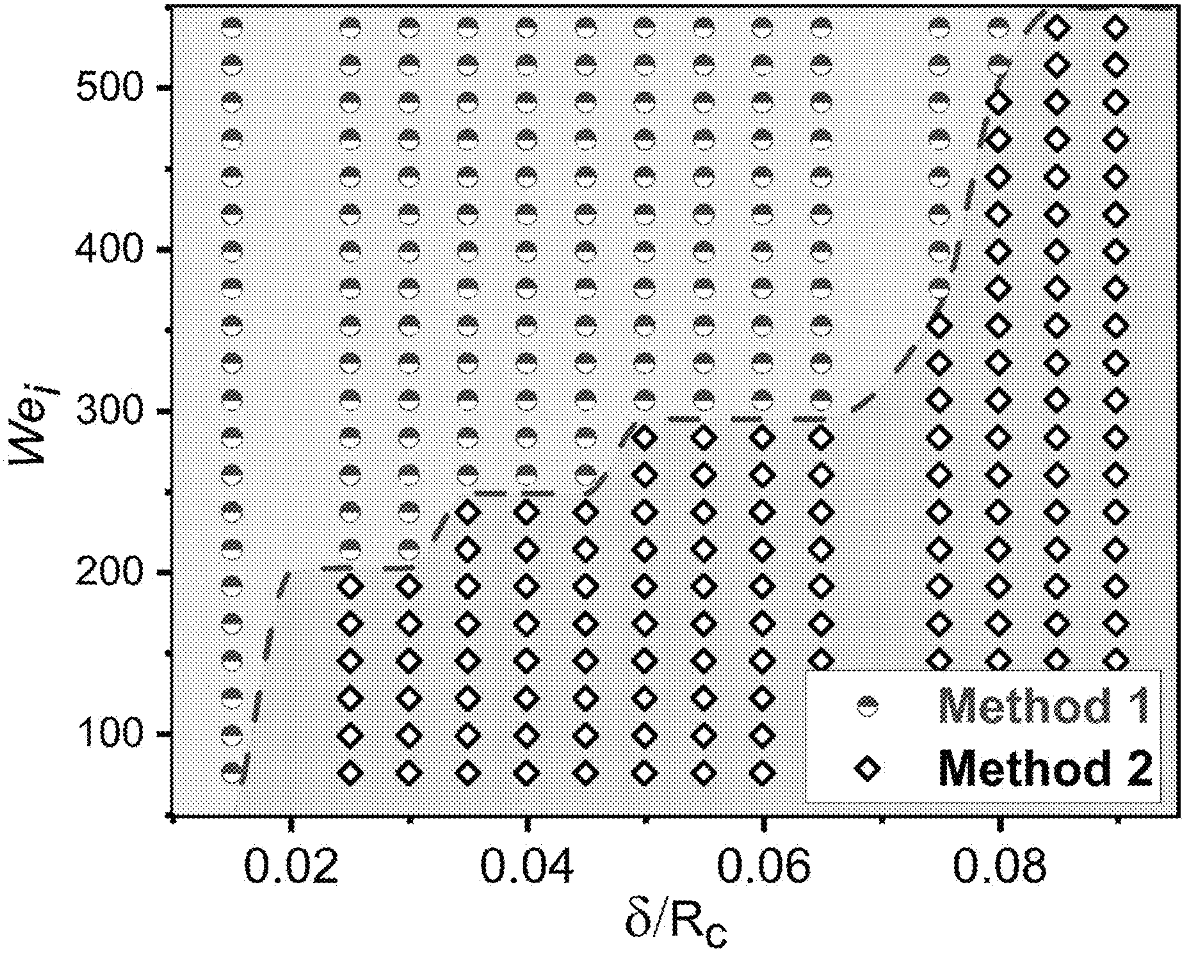
FIG. 3 depicts a regime map showing the regions of applicability of Method 1 and Method 2 of FIG. 1. The dashed line demarcates the two regimes. Encapsulation is achieved by Method 1 above the dashed line, while operating below the dashed line leads to encapsulation by Method 2.

Thermodynamic favorability may not completely dictate the outcome of a dispensed core material (as described herein, e.g., Method 2) or an impacted core material (i.e., as previously reported; e.g., Method 1), as it only considers the energetic suitability of the equilibrium configuration at the encapsulated state and does not account for the irreversible non-equilibrium process during the interaction of the core material with the interfacial material layer. The viscous dissipation during the core material's journey through the interfacial material layer; and competition between the momentum of the dispensed core material, the viscous resistance, and the restorative interfacial forces at the deformed $L_2$-$L_3$ interface, dictates whether encapsulation occurs by Method 1 as previously reported[1], or via the interfacial-trapping Method 2 as described herein. Once the liquid triad satisfies the thermodynamic threshold for stable encapsulation, encapsulation by Method 1 occurs if the kinetic energy of the impacting core material is adequate to overcome the viscous resistance and the interfacial forces offered by the interfacial material layer; and the encapsulation by Method 2 occurs when the kinetic energy of the impacting core material is inadequate to overcome the viscous resistance and the interfacial forces offered by the interfacial material layer. In FIG. 3, a non-dimensional experimental regime for encapsulation is identified in terms of the impact Weber number ($We_i$), and interfacial film thickness non-dimensionalized with respect to the diameter of the core material ($\delta/R_c$). In the examples described herein, $We_i$ is varied in discrete intervals between 75-550 by changing the vertical separation H between the interfacial material layer and the dispensing needle containing the core material. For lower δ, the oncoming core material may penetrate through the interfacial material layer even with low $We_i$ due to the low viscous resistance offered by the interfacial material layer. Therefore, upon impact, encapsulation is achieved by Method 1, where the core material is encapsulated by the interfacial material layer inside the host fluid. For a higher value of $\delta/R_c$, a higher $We_i$ is required for encapsulation by Method 1, owing to the greater kinetic energy needed to overcome the viscous energy barrier. Consequently, a gradual transition from Method 1 to Method 2 is experimentally observed in the regime map presented in FIG. 3 with an increase in $\delta/R_c$. The dashed line, demarcating the two regimes, experimentally maps the critical Weber number, $We_{cr}$, as a function of δ.

Beyond an interfacial PDMS film thickness δ~123 μm (and a corresponding $\delta/R_c$~0.08), encapsulation was achieved only by interfacial trapping (Method 2 as described herein) for the range of $We_i$ explored in the examples described herein. In previously reported[1] Method 1 underwater formation of encapsulated materials was demonstrated using canola oil as the interfacial material layer. The study demonstrated encapsulation by complete interfacial penetration (analogous to Method 1) for a much higher $\delta/R_c$ (~2.8) with a lower $We_i$ (~160). This is an expected outcome as PDMS is ~55 times more viscous than canola oil. This high viscosity significantly increases the viscous resistance offered by the PDMS interfacial material layer, causing interfacial trapping at a much lower interfacial film thickness. However, with PDMS as the interfacial layer, the transition to interfacial trapping at low $\delta/R_c$ is not a functional bottleneck and could be advantageous for two reasons. First, with suitable structural stability, a capsule with a thin shell is often more desirable in several applications due to improved dosage efficiency and release profile. Using PDMS as the shell-forming material allows the formation of stable capsules even in aggressive environments despite having a relatively thin shell layer. Second, when the impinging core material is trapped at the interface, the heat curability of PDMS allows extraction and subsequent handling of the encapsulated material(s). Further, there is no upper limit for interfacial film thickness for the applicability of Method 2. Successful interfacially-trapped encapsulation of core materials may be possible with an interfacial material thickness δ as high as 0.77 mm (corresponding $V_{PDMS}$=1 ml). Thus, using PDMS as the interfacial material may facilitate the formation of capsules with shell thickness control without restricting the kinetic energy requirement.

Practical Use Cases—Development of Robust, Multifunctional Capsules

Figure 4:
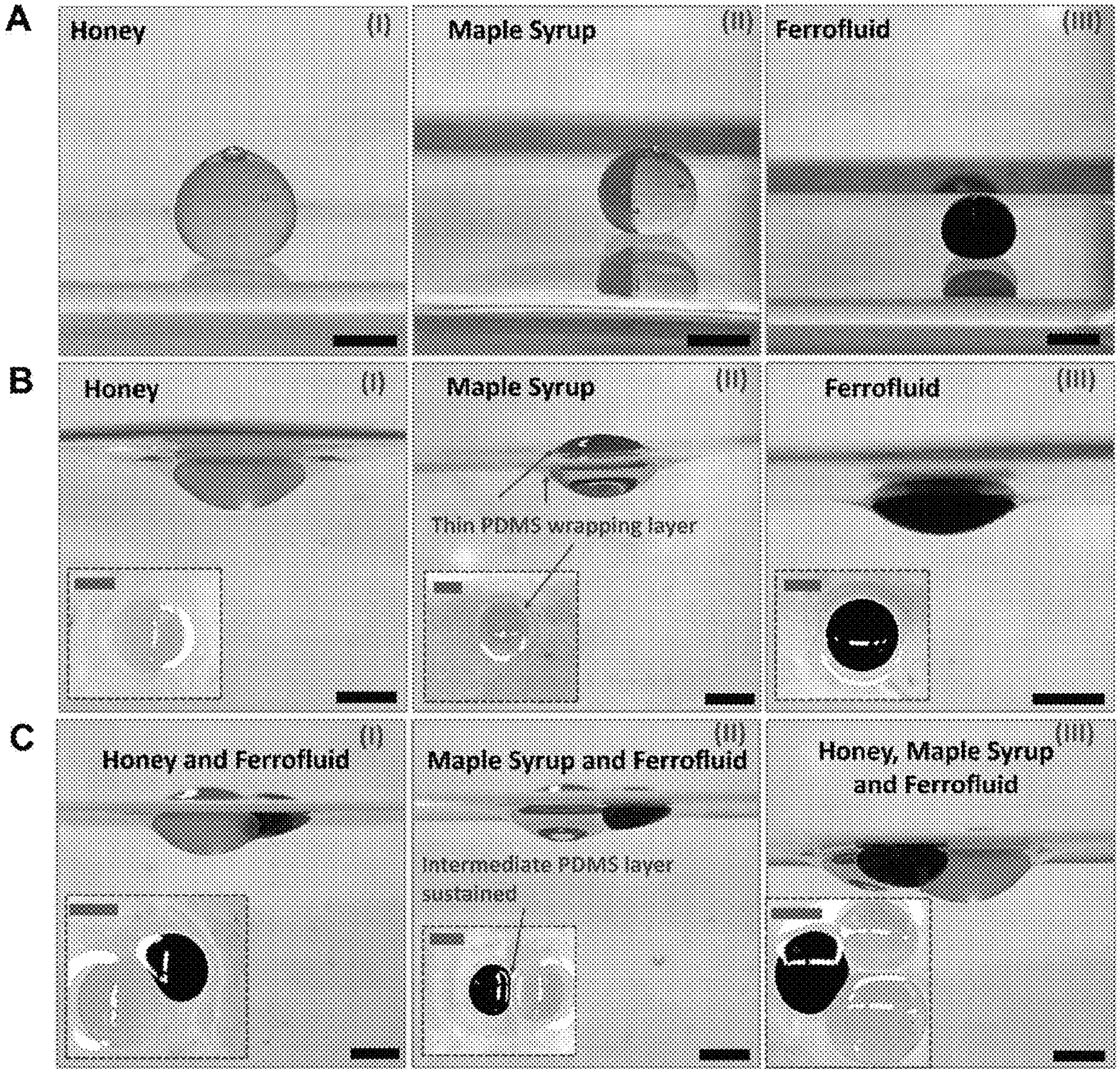
FIG. 4 depicts the demonstration of the use of the method described herein involving miscible core material-host fluid combinations. (A) Underwater formation of capsules using Method 1 of FIG. 1 with a thin PDMS shell containing (I) honey, (II) maple syrup, and (III) PEG-based ferrofluid as core materials. Impact height H=46.6 cm. (B) Formation of interfacially trapped capsules using Method 2 of FIG. 1 containing (I) honey, (II) maple syrup, and (III) PEG-based ferrofluid as core materials. Impact height H=16.6 cm. (C) Encapsulation using Method 2 of FIG. 1 with multiple interfacially trapped core materials leading to Janus configuration containing (I) Honey and PEG-based ferrofluid, (II) Maple syrup and PEG-based ferrofluid, and (III) Honey, maple syrup, and PEG-based ferrofluid. The core materials were dispensed sequentially on the floating interfacial material layer from proximity (H~5 mm), maintaining $We_i$<10. Insets show the top view of the corresponding cases. In all cases, 50 µl of freshly prepared PDMS was used to create the floating interfacial material layer, resulting in a thin interfacial material layer with thickness δ=38.6 µm. The scale bar represents 2 mm throughout the figure.

Applications for interfacially trapped encapsulated core materials prepared by the method as described herein (e.g., Method 2) may include protecting the core materials by safeguarding them from aggressive (e.g., reactive, deteriorating, dissolving, etc.) environments and/or preventing unwanted release. FIG. 4 depicts an example of one such application of the interfacially-trapping encapsulation method described herein (e.g., Method 2).

Three test liquids were used as core materials: two food ingredients (honey and maple syrup) and a PEG-based ferrofluid suspension that offers several functional advantages, including magnetic manipulation and analyte targeting. These core materials were chosen so that they were all miscible in the used host fluid (e.g., deionized water), allowing for the evaluation of the protection provided to a core material upon encapsulation.

Panel A in FIG. 4 shows an example of an impact-driven underwater formation of PDMS-encapsulated stable capsules of the three tested core materials prepared using Method 1. A relatively high impact height of H=46.6 cm was used to ensure that the impinging core materials had sufficient kinetic energy $KE_{impact}$ to penetrate through the interfacial material layer. After penetration, all three core materials were encapsulated by a PDMS layer. A predetermined volume of the interfacial material $V_{PDMS}$=50 μL was used to create the floating interfacial material layer, resulting in a thin shell with thickness δ=38.6 μm. Further, it was noted that despite the thinness of the PDMS wrapping layer, the encapsulated material remained stable in host fluid (e.g., deionized water), with no visual signs of perishing/dissolving of the miscible core material in host fluid observed.

Panel B of FIG. 4 depicts an example of interfacially-trapped encapsulated core materials (herein described Method 2), where the respective core materials of (I) honey, (II) maple syrup, (III) PEG-based ferrofluid were dispensed from height H=16.6 cm, achieving encapsulation by interfacial trapping. Each core material was dispensed on the floating layer of interfacial material from close proximity (H~5 mm), maintaining $We_i<10$. A predetermined volume of the interfacial material $V_{PDMS}=50$ µL was used to create the floating interfacial material layer, resulting in a thin shell with thickness δ=38.6 µm. Formation of a PDMS shell was observed, as shown in the digital photographs presented in panel B of FIG. 4. A thin interfacial material layer of PDMS was used; however, encapsulation by interfacial trapping could also be realized for higher PDMS layer volumes (as shown in the regime map in FIG. 3), allowing thicker cured capsules on demand to be obtained, as shown in FIG. 5.

Additionally, as shown in panel C of FIG. 4, the method of interfacial trapping encapsulation as described herein (e.g., Method 2) was further extended to simultaneously encapsulate multiple core materials of different compositions. In each case, the core material was dispensed on the floating layer of interfacial material from close proximity (H~5 mm) maintaining $We_i<10$. A predetermined volume of the interfacial material $V_{PDMS}=50$ µL was used to create the floating interfacial material layer, resulting in a thin shell with thickness δ=38.6 µm. This allowed for the formation of encapsulated Janus droplets with multiple functionalities in the same encapsulated material. To achieve this, the various core materials were dispensed on top of the floating interfacial material layer one after another from close proximity. Once dispensed, the core materials became individually encapsulated by the PDMS interfacial material layer in a trapped state owing to their adherence to the thermodynamic conditions for wrapping. Additionally, the low $KE_{impact}$ associated with the proximal dispensation coupled with the high viscosity of the PDMS appeared to prevent complete drainage of the intermediate PDMS shell between the neighboring core materials, thereby preventing unwanted direct interaction and/or contact and subsequent coalescence between the different core materials. As a result, multiple core materials with different physicochemical properties were individually encapsulated inside the same outer shell layer (PDMS). This led to the formation of compound droplets with Janus configuration, where multiple core materials individually carried different functionalities without interacting among themselves while residing in the same outer shell layer (PDMS).

Curing of Encapsulated Material

Figure 5:
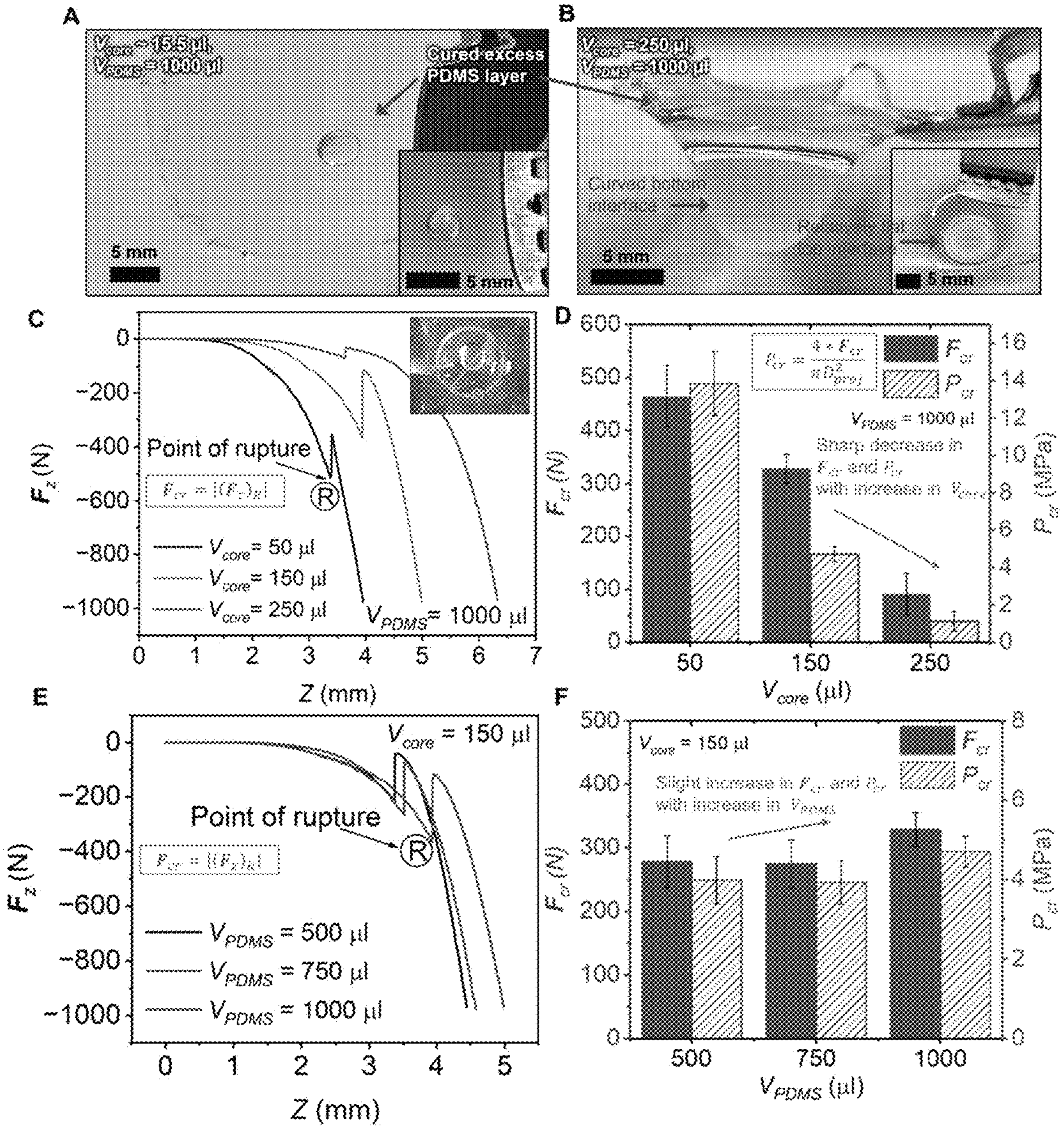
FIG. 5 depicts curing and mechanical characterization of the interfacially trapped (Method 2) capsules. (A-B) show images of the cured capsules containing laser oil core material encapsulated in a PDMS interfacial material layer with $V_{core}$~15.5 µl and 250 µl, respectively. The volume of the PDMS interfacial material layer is kept fixed at $V_{PDMS}$=1000 µl. (B) shows the side-view of the cured capsule, while the capsule had to be tilted upward while capturing the image presented in (A), as the side-view projection could not reveal the contour of the encapsulated drop owing to the smaller size of the core material. The insets show the corresponding top views of the cured capsules. (C-D) shows the mechanical characterization of the cured capsules. (C) shows the plots of reaction force, $F_z$ vs. traversal distance, z recorded by a load cell on a tribometer during compression testing of cured capsules for three different $V_{core}$ with a fixed $V_{PDMS}$. (D) shows a tabulation of the crushing force, $F_{cr}$, and crushing strength, $P_{cr}$ of the capsules corresponding to the data in (C). (E-F) shows the mechanical characterization of the cured capsules. (E) shows the plots of reaction force, $F_z$ vs. traversal distance, z recorded by a load cell on a tribometer during compression testing of cured capsules for three different $V_{PDMS}$ with a fixed $V_{core}$. (F) shows a tabulation of the crushing force, $F_{cr}$, and crushing strength, $P_{cr}$ of the capsules corresponding to the data in (E)

FIG. 5 shows the curing and subsequent characterization of the materials encapsulated by the interfacial trapping mechanism (e.g., Method 2). The encapsulated materials were formed by dispensing laser oil core materials proximally ($We_i<10$) on top of a floating PDMS interfacial material layer and subsequently heating the experimental cuvette on a hot plate overnight at 70° C. The volume of the core material ($V_{core}$) and the PDMS interfacial material layer ($V_{PDMS}$) may both be varied over a broad range to suit different size and hardness requirements of the final capsules. The curing experiment examples described herein used the following ranges as 15.5 µl≤$V_{core}$≤250 µl and 50 µl≤$V_{PDMS}$≤1000 µl.

FIGS. 5A and 5B show the experimental images of the cured capsules for two different $V_{core}$, 15.5 µl and 250 µl, respectively, for a fixed volume of PDMS interfacial material layer, $V_{PDMS}$=1000 µl. Heating the experimental cuvette after proximally dispensing the core material onto the interfacial material layer leads to the solidification of the entire interfacial material layer with the core material trapped inside. FIGS. 5A and 5B show the cured interfacial material layer after removing it from the experimental cuvette. The solidified excess interfacial material layer around the cured encapsulated core material is visible in FIGS. 5A and 5B. Once extracted from the cuvette, this excess PDMS interfacial material layer could be trimmed off. FIGS. 5A and 5B show that the interfacially-trapping encapsulation method described herein (Method 2) can form capsules of different dimensions and/or core material-to-shell volume ratios.

Note that, in the interfacially trapped configuration (e.g., Method 2), the floating PDMS interfacial material layer that encapsulates the core material has two dissimilar interfaces, namely, the top air-PDMS interface and the bottom PDMS-water interface. Once the core material was dispensed, the PDMS-water interface sagged downward due to the combined weight of the core drop and the interfacial material layer. The sagging became prominent when the volume of the core material $V_{core}$ was high (see FIG. 5B). As a result, the bottom interface of the encapsulated material attained a higher curvature than the relatively flatter top interface, which was sustained after the cured (shell-hardened) material was extracted from the experimental cuvette, as shown in the inset of FIG. 5B. Once cured, the shell was found to withstand normal handling, including exposure to drying under hot air, repeated hand-to-hand transfer, and/or shaking and/or tumbling inside a bottle. The encapsulated material remained stable, with no visible sign of perishing or leakage of the core material.

For compressive stress testing, the cured capsule was first placed on a clean glass slide with the cured capsule's flatter top interface facing the glass slide. Subsequently, the load cell with a maximum load capacity of 1000 N was brought close to the cured capsule. Then the load cell was made to traverse downward at a velocity of 0.05 mm/s using the tribometer's computer-controlled program, which lead to squeezing of the cured capsule. The reaction force, $F_z$, was recorded by the load cell as a function of the traversal distance, z. The reaction force, $F_z$ was directed upward, opposite to the direction of z (downward), which is why $F_z$ carries a negative sign. FIG. 5C shows that $|F_z|$ increases initially with increasing z. However, at one point, a sharp reduction in the magnitude of $F_z$ ($|F_z|$) was observed. This point corresponded with the rupture of the shell, which led to leakage of the encapsulated core material. The trapped core material was pressurized as the load cell squeezed the capsule. Eventually, rupture led to a sudden release of this pressure, manifested in a sharp reduction in the reaction force. Point R, marked in FIG. 5C, indicates the point of rupture. The absolute magnitude of the reaction force recorded at the point of rupture is termed the crushing force ($F_{cr}$). After the sudden reduction in $|F_z|$ immediately following the rupture, $|F_z|$ again increases with increasing z as the load cell continued compressing the broken capsule until the maximum load capacity of 1000 N was reached.

In FIG. 5C shows two distinct trends in the $F_z$ vs. z plots with varying $V_{core}$. First, at a higher $V_{core}$, the slope of the $F_z$ vs. z curve before rupture is low. This is because a higher volume fraction of the liquid core in the cured capsule leads to a more deformable capsule. As a result, during the downward traversal of the load cell, the capsule was deformed relatively easily, leading to dissipation of the downward applied compressive load. In the case of a higher $V_{core}$, the load cell experiences a lower upward reaction force, $F_z$, for the same traversal distance, z, compared to capsules with a lower $V_{core}$, which is reflected in the slope of the $F_z$ vs. z curves. Second, $F_{cr}$ decreases with increasing $V_{core}$. For the same $V_{PDMS}$, increasing $V_{core}$ corresponds to a lower volume fraction of the solidified shell material in the cured capsule (e.g., a thinner shell). It leads to a lower resistance to crushing under compressive load, manifested in the reducing trend of $F_{cr}$ with increasing $V_{core}$. The crushing strength (pressure), $P_{cr}$, may be estimated by dividing $F_{cr}$ with the projected cross-sectional area of the droplet, as follows, $$P_{cr} = \frac{4 * F_{cr}}{\pi D_{proj}^2}.$$

The projected diameter, $D_{proj}$ of the capsule was obtained from the experimental image of the cured capsule, as shown in the inset of FIG. 5C. Both $P_{cr}$ and $F_{cr}$ are plotted side-by-side as a bar graph in FIG. 5D for the three different $V_{core}$ values as described herein, and there was a consistent, decreasing trend of both the parameters with increasing $V_{core}$.

FIGS. 5E and 5F show the influence of the variation of the volume of the shell material (PDMS) in the range 500 μl≤$V_{PDMS}$≤1000 μl on the reaction force, $F_z$, the crushing force $F_{cr}$ and the crushing strength (pressure), $P_{cr}$ when the core material volume was kept fixed $V_{core}$=150 μl. The recorded force ($F_z$) vs. displacement of the load cell (z) plots with varying $V_{PDMS}$ is shown in FIG. 5E, while FIG. 5F summarizes the variation of crushing force, $F_{cr}$, and crushing strength, $P_{cr}$ with different tested $V_{PDMS}$. It is evident that the change in $V_{PDMS}$ has a much less pronounced effect on the mechanical properties of the cured capsules in comparison to changes in $V_{core}$. As we increased $V_{PDMS}$ from 500 μl to 1000 μl. For undergoes a slight increment of ~18.1%. The higher sensitivity of $F_{cr}$ and $P_{cr}$ towards $V_{core}$ is not a surprising outcome. Any change in $V_{core}$ is directly manifested in its entirety in the morphology of the interfacially trapped capsule. On the contrary, $V_{PDMS}$ being the volume of the floating interfacial material layer and not the shell volume of the encapsulated capsule, changes in $V_{PDMS}$ is reflected over the entire surface area of the interfacial layer (which can be assumed equal to the free-surface area of the host fluid. As we are utilizing only a small fraction (<10%) of the free surface area of the interfacial layer to generate the interfacially trapped capsules, the effect of changing $V_{PDMS}$ on the morphology of the resulting capsules remains significantly less pronounced.

Conclusions

A platform for the formation of capsules with core-shell morphology using an interfacial-trapping encapsulation framework is described herein. A complex interplay between the force associated with the momentum, $p_{in}$, the viscous dissipation, $F_{visc}$, and the restorative interfacial tension force, $F_\gamma$ acting on a deformed $L_2$-$L_3$ interface, dictates the interfacially-trapped pathway to encapsulation. For interfacial trapping (e.g., Method 2), the $L_2$-$L_3$ interface undergoes an initial downward elongation phase. Then the interface retracts upward toward its initial unperturbed state due to $F_\gamma$ once $KE_{impact}$ is dissipated by the viscous resistance. A non-dimensional experimental regime for the occurrence of encapsulation via interfacial-trapping as described herein (e.g., Method 2) vs. encapsulation via interfacial-penetrating as discussed herein (e.g., Method 1) in terms of $We_i$ and the non-dimensional interfacial material layer thickness ($\delta/R_c$) is described herein. The critical Weber number, $We_{cr}$, which is a function of δ, demarcates the transition between these two outcomes.

Stable capsules can be formed as long as the participating triplet (core material, shell material, and host fluid) adheres to an interfacial energy condition. The shell may safeguard core materials despite their miscibility with the host fluid. Interfacial-trapping encapsulation (e.g., Method 2) may also be implemented to create multifunctional Janus capsules that contain multiple core materials within one shell. Subsequently, the extraction of the interfacially trapped capsules was demonstrated via heat curing of the PDMS outer shell. The interfacially trapped capsule with $V_{core}$=150 μl and $V_{PDMS}$=1000 μl possessed a crushing strength value of $P_{cr}$~4.7 MPa. Increasing $V_{core}$ with a fixed $V_{PDMS}$ led to a reduction in both crushing force, $F_{cr}$, and crushing strength, $P_{cr}$, owing to a decrease in shell thickness of the cured capsules.

Example 2: Liquid-Liquid Encapsulation Via Interfacial Penetration of a Compound Core Droplet

Materials

Four liquids are used and denoted as follows: inner core material (liquid $L_{c,i}$), outer core material (liquid $L_{c,o}$), interfacial material forming the outer shell (liquid $L_s$), and host fluid (liquid $L_h$), on top of which the interfacial material was dispensed. The subscripts "c,i" and "c,o" indicate the inner and outer core, respectively. If not otherwise mentioned, a class of laser liquid—a mixture of silicanes and polyphenol ethers with a water solubility of <0.1% (Product Code: 57B63, Cargille Laboratories Inc., Cedar Grove, NJ, USA) was used to form the outer core material. The relevant material properties are as follows: density $\rho_{c,o}$=1900 kg/m$^3$, dynamic viscosity $\mu_{c,o}$=1024 mPas, liquid-air surface tension $\gamma_{c,o}$=50 mN/m, and liquid-water interfacial tension $\gamma_{c,o-h}$=39.4 mN/m. Three different interfacial material layers ($L_s$)—canola oil, silicone oil, and oil-based ferrofluid are used as the interfacial material layer ($L_s$). The host liquid was deionized (DI) water (purified by Milli-Q, MilliPoreSigma, Ontario, Canada) with density $\rho_3$=1000 kg/m$^3$, dynamic viscosity $\mu_3$=1 mPas and liquid-air surface tension $\gamma_3$=72 mN/m.

Methods

The experiments were conducted in a distortion-free glass cuvette (Product Code: SC-02, Krüss GmbH, Hamburg, Germany) of inner dimension 36 mm×36 mm×30 mm with a 2.5 mm wall thickness. Before each experiment, the glass cuvette is thoroughly cleaned by soaking and subsequent ultrasonication (Branson 5800, Emerson Electric Co., USA) in hexane for 30 min. After that, the cuvette is thoroughly rinsed with DI water and acetone, followed by drying with compressed nitrogen. Next, the cleaned cuvette was treated in air plasma (PE-25, PLASMA ETCH, USA) for 10 min. Then, the cuvette was placed over a vertically movable stage (Kruss GmbH, Hamburg, Germany). At first, the cuvette was partially filled with 20 ml of the host liquid (DI water). Subsequently, a predetermined volume of the interfacial material layer was dispensed on top of the water bath from proximity using a pipette (DiaPETTE, Canada) and allowed to spread uniformly for ~2 min, resulting in the formation of a thin interfacial layer (i.e., which acts as the outer shell layer) of respective thickness. Using the linear translating stage, the dispenser was taken to the predetermined height, H. The impact height in the case of double-layered encapsulation varies between H=5 cm to H=46 cm. A Y-junction flow arrangement was employed to generate a compound droplet. Here, the outer core material (laser oil) was pushed through the vertically oriented microtip (inner diameter of 2 mm) attached to a syringe. At the same time, the inner core drop (ethylene glycol) was introduced from the side using a flat-tipped stainless-steel needle (gauge 25, part no. 7018339, Nordson EFD, USA) of internal diameter 0.25 mm mounted on a 1 ml NORM-JECT syringe. Using a programmable syringe pump (Chemyx Fusion 4000). Then, the compound core material was dispensed by pumping laser oil using the programmable syringe pump (Chemyx Fusion 4000) at a controlled rate as desired. Upon detachment from the microtip, the compound core material accelerates downward due to gravity and encounters the interfacial material layer. Owing to sufficient kinetic energy, the compound core material overcomes the interfacial and viscous barriers and penetrates through the interfacial material layer. This process results in the wrapping of the compound core material by the interfacial material layer. The complete dynamics of the encapsulation process were captured using a high-speed camera (Photron FASTCAM Mini AX200) at 6400 fps.

Results and Discussion

Figure 6:
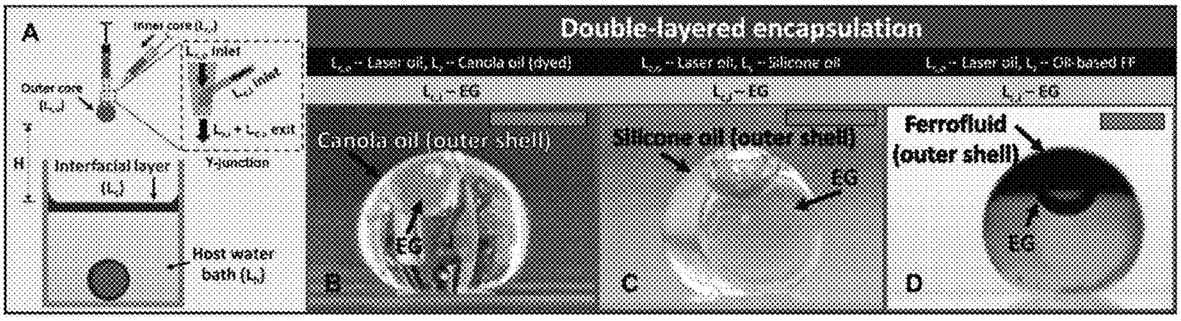
FIG. 6 depicts a schematic representation of the formation of liquid-liquid encapsulation via interfacial penetration of a compound droplet through a floating interfacial material layer. (A) shows the schematic of the process where a Y-junction geometry facilitates the wrapping of the inner core material ($L_{c,i}$) inside an outer core liquid material ($L_{c,o}$) forming a compound core material. The compound core material impinges on the interfacial material layer ($L_s$) resulting in the formation of double layered encapsulation. (B-D) depicts the final encapsulated material where ethylene glycol is used as the inner core material ($L_{c,i}$) and laser oil is used as the outer core material ($L_{c,o}$) for (B) canola oil as the interfacial material layer ($L_s$), (C) silicone oil as the interfacial material layer ($L_s$) and (D) oil-based ferrofluid as the interfacial material layer ($L_s$) with a scale bar of 2 mm throughout.

The practical utility of efficient encapsulation lies in providing efficient protection to target analytes by safeguarding them in aggressive surroundings and preventing unwanted release. FIG. 6 demonstrates the applicability of the demonstrated technique in encapsulating the compound core material inside the host fluid bath.

The schematic in FIG. 6A depicts the liquid-liquid encapsulation process where a Y-junction geometry facilitates the wrapping of the inner core material ($L_{c,i}$) inside an outer core liquid material ($L_{c,o}$), forming a compound core material. The compound core material impinges on the interfacial material layer ($L_s$) resulting in the formation of a shell of the interfacial material around the compound core material.

Ethylene glycol and laser oil were used as the inner core material ($L_{c,i}$) and outer core material ($L_{c,o}$), respectively. Three liquids were used as the interfacial material layer-canola oil of volume $V_{L_s}$=120 μl (FIG. 6B), silicone oil of volume $V_{L_s}$=90 μl (FIG. 6C), and oil-based ferrofluid of volume $V_{L_s}$=200 μl (FIG. 6D). In each case in FIG. 6(B-D) the impinging compound core material has sufficient kinetic energy to penetrate through the interfacial material layer. After successful penetration, the compound core material in each case was wrapped by the respective interfacial material layers, as shown in FIG. 6(B-D). Further, it was noted that despite the thinness of the outer shell layer, the encapsulated compound core material remained stable in host water bath, and no sign of perishing/dissolution of the miscible inner core in water could be observed.

Conclusions

In summary, this work presents a holistic framework of liquid-liquid encapsulation to fabricate encapsulated cargo via interfacial penetration of a compound core material using the combination of Y-junction and impact-driven liquid-liquid encapsulation. Compound core materials consisting of a liquid inner core and another liquid outer core are generated using the Y-junction geometry. Impingement of the compound core material on a liquid interfacial material layer (shell) floating on the host fluid results in wrapping the compound core material by the interfacial material layer, forming the encapsulated material. Using this technique, stable wrapping of smaller and aqueous cores was demonstrated, which is challenging to achieve in the previously demonstrated impact-driven liquid-liquid encapsulation[1,2]. To demonstrate the universality of the technique, various interfacial layer materials (e.g., canola oil, silicone oil and oil-based ferrofluid) were used to generate the encapsulated material. Incorporation of an oil-based ferrofluid as the interfacial material layer, a magneto-responsive encapsulated material was generated that can be exploited for magnet-assisted manipulation.

REFERENCES

1. Misra, S., Trinavee, K., Gunda, N. S. K. & Mitra, S. K. Encapsulation with an interfacial liquid layer: Robust and efficient liquid-liquid wrapping. *J. Colloid Interface Sci.* 558, 334-344 (2020).
2. Mitra, S., Gunda, N. S. K., Misra, S. & Trinavee, K. Liquid encapsulation method and compositions and uses related thereto. (2022).
3. Yin, S. et al. Triple-layered encapsulation through direct droplet impact. *J. Colloid Interface Sci.* 615, 887-896 (2022).
4. Misra, S., Banerjee, U. & Mitra, S. K. Liquid-Liquid Encapsulation: Penetration vs. Trapping at a Liquid Interfacial Layer. *ACS Appl. Mater. Interfaces* 15, 23938-23950 (2023).
5. Ushikubo, F. Y., Birribilli, F. S., Oliveira, D. R. B. & Cunha, R. L. Y- and T-junction microfluidic devices: effect of fluids and interface properties and operating conditions. *Microfluid. Nanofluidics* 17, 711-720 (2014).
6. Kim, D., Kim, S.-H. & Park, J. Y. Floating-on-water Fabrication Method for Thin Polydimethylsiloxane Membranes. *Polymers* 11, 1264 (2019).

We claim:

1. A method of forming an encapsulated core material, comprising:

providing an interfacial material layered on a host fluid;
dispensing a core material onto the interfacial material;
interfacially trapping the core material in the interfacial material; and
forming a shell of interfacial material around the interfacially-trapped core material that protects the core and forms the encapsulated core material.

2. The method of claim 1, further comprising curing the shell of the encapsulated material while interfacially trapped by exposing the encapsulated material to heat or UV radiation, and forming a cured encapsulated material.

3. The method of claim 2, further comprising isolating the cured encapsulated material from the interfacial material or host fluid.

4. The method of claim 1, wherein the core material has a density less than the density of the host fluid.

5. The method of claim 1, wherein providing the interfacial material comprises dispensing a volume V of the interfacial material on the host fluid.

6. The method of claim 1, wherein accelerating the core material comprises dropping the core material onto the interfacial material from a height H above the interfacial material wherein the height H is ≥0 mm, or about 0 mm to about 1000 mm, or actuating the core material onto the interfacial material.

7. The method of claim 1, wherein dispensing the core material comprises placing the core material onto the interfacial material.

8. The method of claim 1, wherein interfacially trapping the core material in the interfacial material requires $\gamma_{12}+\gamma_2<\gamma_1$, where $\gamma 1$ is the core material/atmosphere interfacial tension, $\gamma 12$ is the core material/interfacial material interfacial tension, and $\gamma 2$ is the interfacial fluid/atmosphere interfacial tension.

9. The method of claim 1, further comprising:

dispensing at least a second core material onto the interfacial material;

interfacially trapping the at least second core material in the interfacial material;

forming a shell of interfacial material around the at least second core material; and forming an outer shell of interfacial material around the encapsulated core material and the at least second encapsulated core material to form an encapsulated material.

10. A method of forming an encapsulated core material, comprising:

providing an interfacial material layered on a host fluid;

generating a compound core droplet, wherein where the target inner core is enclosed within a high-density outer core using Y-junction geometry; and passing the compound core material with sufficient kinetic energy through the interfacial fluid and into the host fluid such that the interfacial fluid forms a shell around the outer core material that protects the outer and inner core and forms the encapsulated core material.

11. The method of claim 10, wherein the compound core material has an effective density $\rho$, the interfacial fluid has a density $\rho_2$ and the host fluid has a density $\rho_3$, and wherein:

$$\rho_2 < \rho_3 < \rho$$

and $$\rho = \beta\rho_{c,i} + (1-\beta)\rho_{c,o}$$

where, $\rho_{c,i}$ and $\rho_{c,o}$ are the densities of the inner core and the outer core, respectively, and $\beta$ is the ratio of the volume of the inner core material to the volume of the total compound core material.

12. The method of claim 10, wherein the formation of stably encapsulated material inside the host bath requires $\gamma_{L_{c,o}-h}-\gamma_{L_{c,o}-L_s}-\gamma_{L_s-L_h}>0$ where, $\gamma_{L_{c,o}-h}$, $\gamma_{L_{c,o}-L_s}$ and $\gamma_{L_s-L_h}$ are the interfacial tension values of outer core/host bath, outer core/interfacial fluid, and interfacial fluid/host bath combinations, respectively.

13. The method of claim 1, wherein the core material is a fluid, and the fluid comprises a liquid, a liquid mixture, a liquid polymer, a liquid polymer mixture, a laser liquid, a liquid agar gel, a liquid gelatin, a liquid cellulose, a liquid food ingredient, a liquid nutrient, an oil, a fish oil, a probiotic, a solution, a pharmaceutical compound, an enzyme, a colloidal liquid, a suspension containing microparticles, nanoparticles, a ferrofluid, a water-treatment compound, a soil-treatment compound, or a combination thereof.

14. The method of claim 1, wherein when the core material is a solid, and comprises a solid mixture, a solid suspension, a gel, an agar gel, a gelatin, a polymer, a cellulose, a nut, a seed, a pharmaceutical compound, an enzyme, a microparticle, a nanoparticle, a ferrofluid, a surfactant, a mineral, a food ingredient, a nutrient, an oil, a fish oil, a probiotic, a water-treatment compound, a soil-treatment compound, or a combination thereof.

15. The method of claim 1, wherein the interfacial material comprises a liquid, a liquid mixture, a liquid polymer, a liquid polymer mixture, a laser liquid, a liquid agar gel, a liquid gelatin, a liquid cellulose, a liquid food ingredient, a liquid nutrient, an oil, a fish oil, a probiotic, a solution, a pharmaceutical compound, an enzyme, a colloidal liquid, a suspension containing microparticles, nanoparticles, a ferrofluid, a surfactant, a mineral, a food ingredient, a water-treatment compound, a soil-treatment compound, or a combination thereof.

16. The method of claim 1, wherein the interfacial material is curable including, but not limited to, cross-linkable or vulcanizable materials and comprises a liquid, liquid mixture, liquid polymer, liquid polymer mixture, laser liquid-liquid agar gel, liquid gelatin, liquid cellulose, oil, silicone oil, solution, suspension, colloidal liquid, ferrofluid, starch-based biopolymers, thiol-ene biopolymers, or a combination thereof.

17. The method of claim 1, wherein the host fluid is a liquid, a liquid mixture, a liquid food ingredient, a liquid polymer, a liquid polymer mixture, a liquid agar gel, a liquid gelatin, a liquid cellulose, a liquid consumer beverage, a liquid nutrient, an oil, a silicone oil, a fish oil, a solution, a suspension, a colloidal liquid, a ferrofluid, water, an aqueous solution, or a combination thereof.

18. A method of forming a multi-layered encapsulated core material comprising a core material and a shell, the method comprising:

providing an interfacial material layer on a host fluid, the interfacial material layer comprising a first and a second interfacial material, the first interfacial material being layered on the second interfacial material and the second interfacial material being layered on the host fluid, passing the compound core material with sufficient kinetic energy through the interfacial layer and into the host fluid, forming a shell of the interfacial material layer around the core material, the shell comprising at least the first and second interfacial material, and thereby forming the multi-layered encapsulated core material.

19. A cured encapsulated material, comprising:

an encapsulated core material comprising a core material encapsulated in a shell, the shell comprising cured interfacial material.

20. The cured encapsulated material of claim 19, in a form:

for delivery of a pharmaceutical compound; and/or for targeted locomotion of the encapsulated material using active stimuli (e.g., magnetic/electric field, acoustics); and/or for delayed release of a pharmaceutical compound; and/or for incorporation in a cosmetic product; and/or for delayed release of an additive in a cosmetic product; and/or for incorporation in an emulsion; and/or for encapsulating a food ingredient; and/or for incorporation in a food product; and/or for quantum-dot light emitting diodes; and/or for controlled reactions; and/or for incorporation in a beverage; and/or for incorporation in confectionary.

* * * * *